United States Patent [19]

Sgro

[11] Patent Number: 5,697,978
[45] Date of Patent: Dec. 16, 1997

[54] PROSTHETIC ELEMENT FOR THE TREATMENT OF INGUINAL HERNIAS, IN PARTICULAR BY THE CELIOSCOPIC ROUTE

[76] Inventor: Jean-Claude Sgro, 42 cours Général de Gaulle, 21000 Dijon, France

[21] Appl. No.: 579,273

[22] Filed: Dec. 27, 1995

[30] Foreign Application Priority Data

Dec. 30, 1994 [FR] France .................. 94 16019

[51] Int. Cl.[6] ............................................ A61F 2/04
[52] U.S. Cl. .................. 623/12; 623/11; 623/13; 606/151; 606/213; 600/37
[58] Field of Search .................. 623/12, 11, 13, 623/14; 606/151, 213; 602/44; 600/37

[56] References Cited

U.S. PATENT DOCUMENTS

| | | | |
|---|---|---|---|
| 2,671,444 | 3/1954 | Pease | 128/82 |
| 4,769,038 | 9/1988 | Bendavid et al. | 623/13 |
| 5,147,374 | 9/1992 | Fernandez | 606/151 |
| 5,254,133 | 10/1993 | Seid | 606/213 |
| 5,456,720 | 10/1995 | Schultz et al. | 606/213 |

FOREIGN PATENT DOCUMENTS 0 621 014 A1  10/1994  European Pat. Off. .

Primary Examiner—John G. Weiss
Assistant Examiner—Francis K. Cuddihy
Attorney, Agent, or Firm—Nikaido, Marmelstein, Murray & Oram LLP

[57] ABSTRACT

A prosthetic element for the treatment of an inguinal hernia by celloscopy is disclosed, comprising an elongate and flexible binding member, and three leaves which are linked to one another by the binding member, each leaf extending away from the binding member, the leaves being made of a biocompatable material which is sufficiently lacunar or porous to support in vivo a tissue implantation or growth, and sufficiently flexible to be folded back on itself and unfolded, one of the leaves having a cutting therethrough culminating in a hole, the leaf being adapted to tightly enclose the spermatic cord after its passage through the hole.

21 Claims, 3 Drawing Sheets

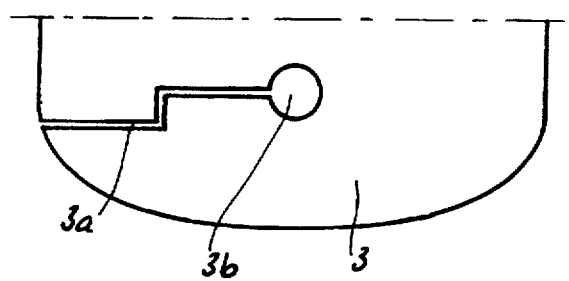
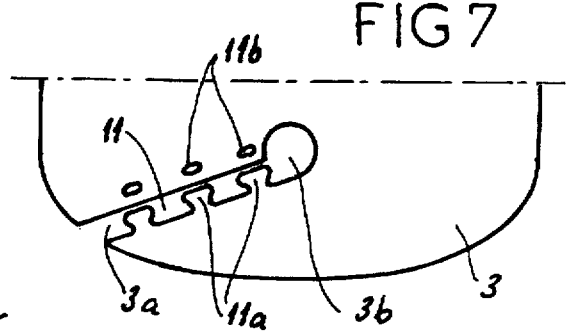
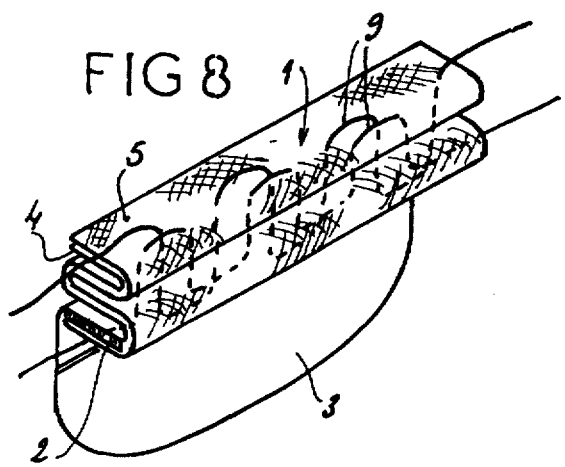
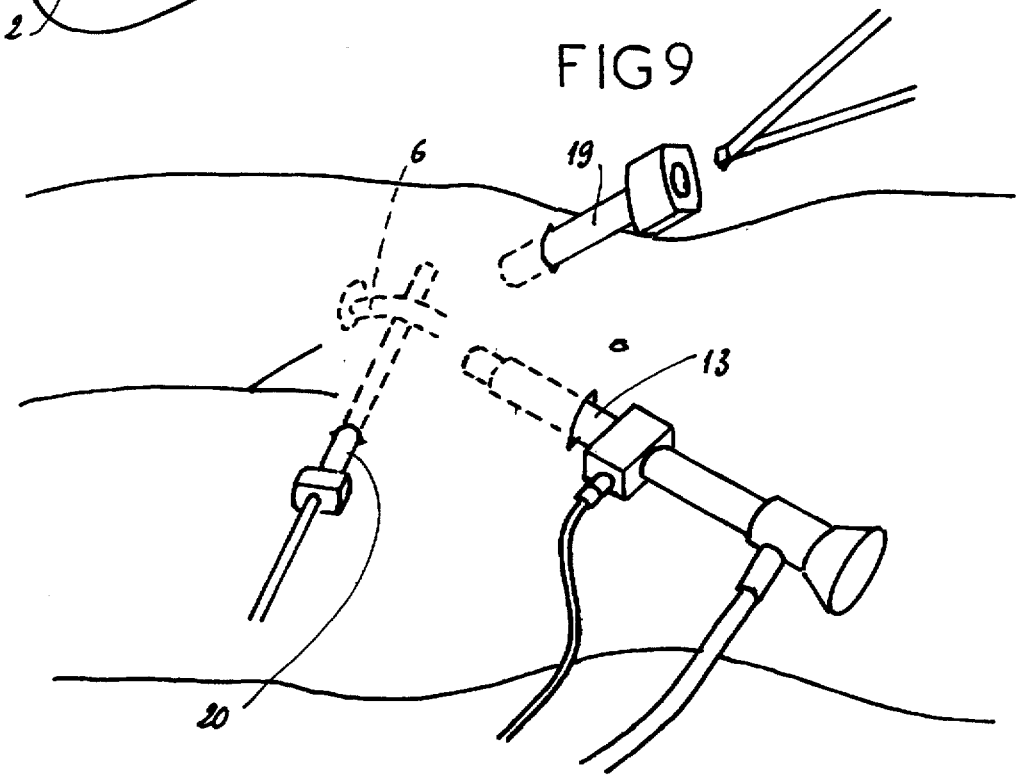

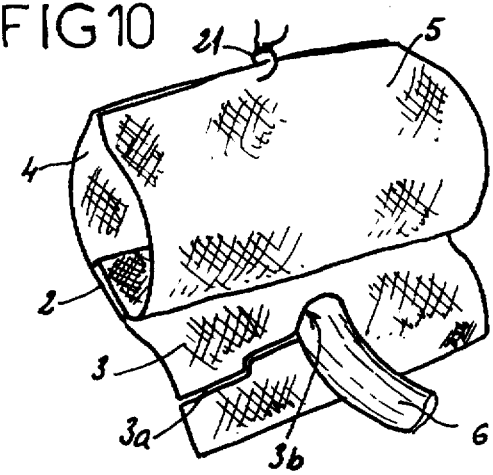
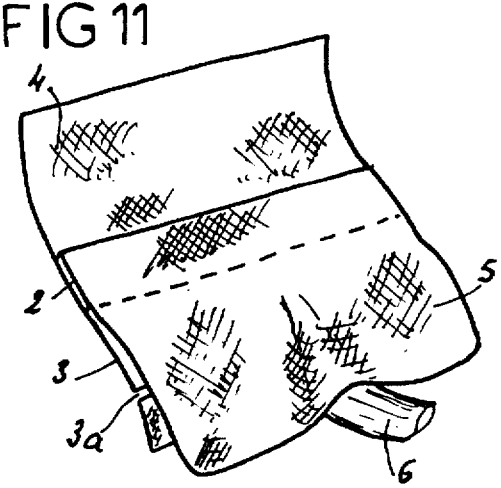
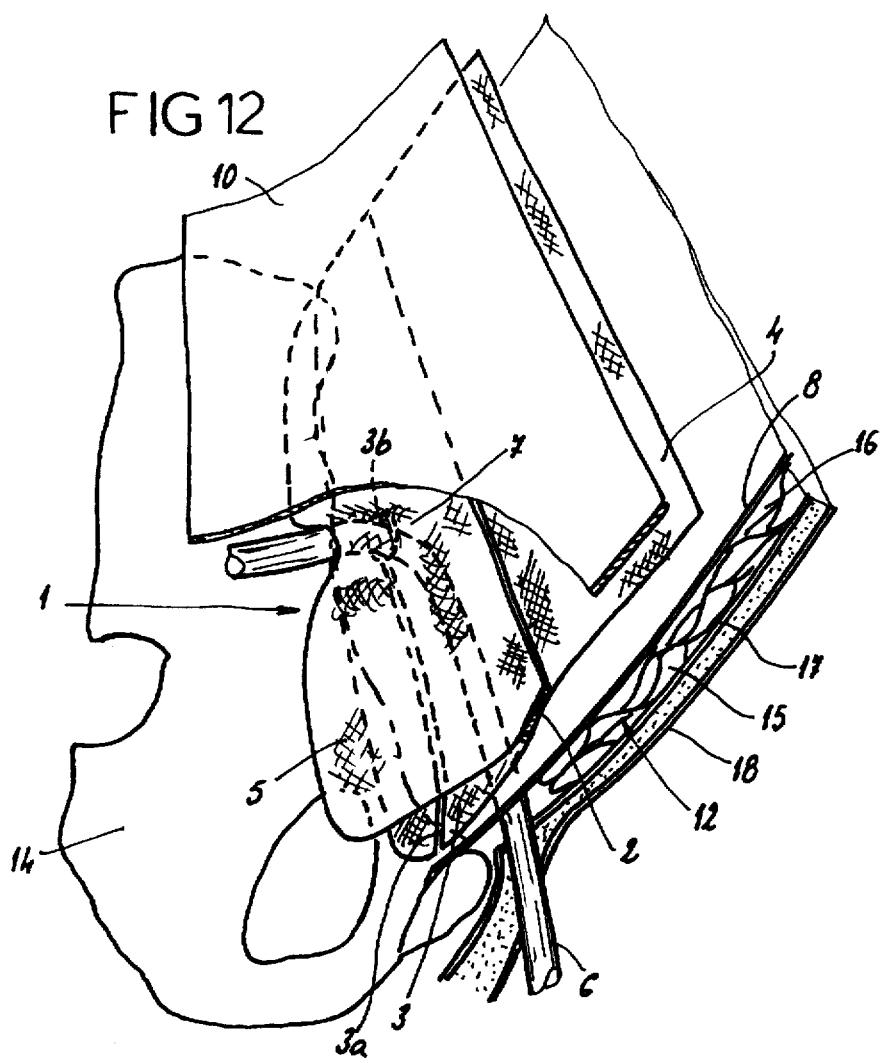

PROSTHETIC ELEMENT FOR THE TREATMENT OF INGUINAL HERNIAS, IN PARTICULAR BY THE CELIOSCOPIC ROUTE

The present invention relates to the surgical treatment of hernias, and more particularly by celioscopy.

In accordance with the document U.S. Pat. No. 4,769,038, for the surgical treatment of an inguinal hernia, using a nonspecified approach, a prosthetic element has already been described which is in the form of a sheet comprising an elongate and flexible binding member, intended to replace the inguinal ligament, and three leaves which are joined to one another via said binding member which is common to them, and each extending away from the latter. Each of these leaves is made of a biocompatible material which is sufficiently lacunar or porous to support in vivo tissue implantation and growth, and sufficiently flexible to be folded back on itself and unfolded at will; this material preferably consists of a textile material. Once this prosthetic element has been implanted, replacing the musculoaponeurotic structures of the inguinal region, its various parts can be distinguished as follows:

the binding member fixed on, or replacing, the inguinal ligament, at one end on the antero-superior iliac crest, and at the other end on the pubic tubercle;

a first, superior and posterior, leaf comprising a cutting which includes a hole for the passage of the spermatic cord; in this way, this leaf tightly encloses said cord, after the two edges of the cutting are connected to one another, outside the abovementioned hole; furthermore, this leaf is fixed on, or replaces, the transversalis fascia;

a second, superior and anterior, leaf fixed on, or replacing, the aponeurosis of the abdominal external oblique muscle;

and a third, inferior, leaf fixed on or replacing Cooper's ligament, and if appropriate on the envelope of the femoral artery.

The prosthetic element previously described and the surgical technique which is associated with it have various disadvantages.

In practice, to avoid any strangulation of the spermatic cord, it is necessary to leave a relatively large interstitial space between the hole, cut in the superior and posterior leaf, and said cord. This interstitial space in practice favours recurrence of the hernia, by a new peritoneal sac sliding along the spermatic cord. This disadvantage is aggravated when the cutting closed back on itself in the superior posterior leaf is distended, or when the internal inguinal opening is very wide, for example in the case of corpulent and obese patients, and provokes a funnel-shaped deformation of the abovementioned leaf.

The same superior and posterior leaf in practice proves insufficient to withstand the pressure of the viscera, and to correctly obstruct the internal inguinal opening.

The surgical technique previously described, a particularly lengthy procedure, remains exclusive to replacing or reconstructing the internal inguinal ligament, and the muscular and abdominal sheaths, namely the transversalis fascia and the aponeurosis of the large oblique muscle. The indication for its use remains extremely rare, since it presupposes the replacement, pure and simple, of anatomical structures destroyed by repeated previous surgery. Also, this technique guarantees only an external protection with respect to the inguinal opening.

In accordance with the French Patent Application 2 704 139, a prosthetic element has been described and proposed which is in the form of a sheet, especially for the treatment of any hernia by celioscopy, comprising at least two leaves made of a material such as defined above and linked to one another in a noncontiguous manner, by a reinforcement, obtained in particular by knitting, and creating an overthickness in relation to the individual thickness of each of said leaves.

The object of the present invention is to remedy the disadvantages of the prior art which have been explained with reference to the document U.S. Pat. No. 4,769,038.

In particular, the subject of the present invention is a prosthetic element of the type which is defined and described in the French Patent Application 2 704 139, which can constitute at one and the same time an inner reinforcement and an obstacle to any recurrence of the hernia at the level of the internal inguinal opening.

A prosthetic element according to the invention combines, in cooperation, the following technical characteristics:

the elongate and flexible binding member has the form of a reinforcement, whose height is adapted to close the internal inguinal opening;

a first leaf, situated in an anterior and inferior position once the prosthetic element has been implanted, is the one intended to tightly enclose the spermatic cord by means of the cutting including the hole for the passage of said cord;

a second leaf, disposed in a superior position once the prosthetic element has been put in place, extends away from the other side of the reinforcement, with a sufficient height to rest on the inner face of the transversalis fascia, with or without attachment to the latter;

and a third leaf, situated in an inferior and posterior position once the prosthetic element has been put in place, with a sufficient height for it to be folded back and held against the inner face of the superior leaf, then folded back against the inferior and anterior leaf, separating the peritoneum from the residual space in the inferior and anterior leaf, between the spermatic cord and the aforementioned hole.

By means of the present invention, it is possible to perform at one and the same time a calibration of the hole providing for the passage of the spermatic cord, and a parietalization of the latter.

In addition, a prosthetic element according to the invention requires only the closure of the cutting, to the exclusion of all other attachments such as staples, although these can be used, however, for certain indications.

The present invention is now described with reference to the attached drawing, in which:

FIGS. 3 through 7 represent from the front, and in a partial view, different embodiments of the inferior and anterior leaf of a prosthetic element according to the invention;

FIG. 8 represents in perspective a prosthetic element according to the invention, in a folded configuration, particularly adapted for passage through a trocar;

FIG. 9 is a diagrammatic and perspective representation of the surgical procedure according to the invention, before insertion, opening-out and positioning of a prosthetic element according to the invention;

FIG. 10 is a diagrammatic representation of the prosthetic element according to the invention, placed around the spermatic cord, before folding the inferior and posterior leaf back against the inferior and anterior leaf;

FIG. 11 represents the prosthetic element according to the invention in place, after the inferior and posterior leaf has been folded back against the inferior and anterior leaf and the spermatic cord;

FIG. 12 represents an anatomical and exploded view of the inguinal region of a patient after implantation and positioning of a prosthetic element according to the invention.

Figure 1:
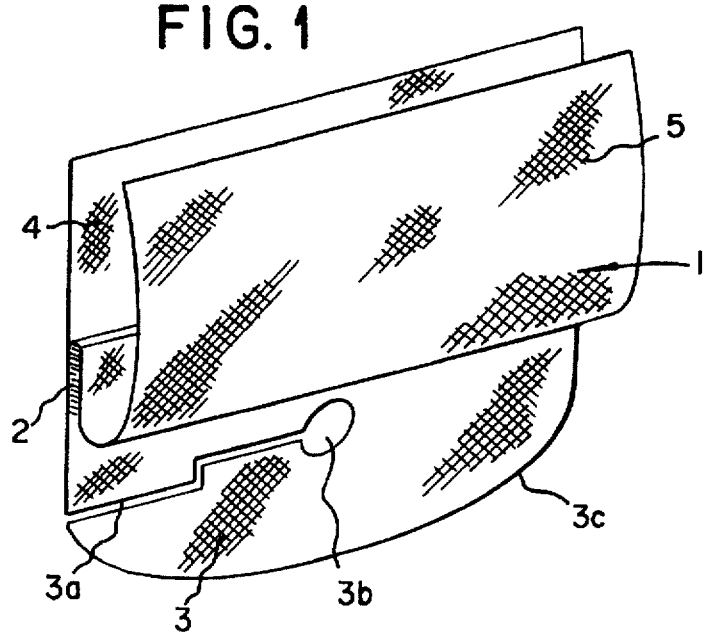
FIG. 1 represents a perspective view of a prosthetic element according to the invention, in its unfolded or opened-out configuration, but with the inferior and posterior leaf folded back against the inner face of the superior leaf.

In accordance with the invention, a prosthetic element 1 presents, in a general manner, the form of a sheet and comprises:

- an elongate and flexible binding member 2 having the form of a reinforcement whose height is adapted to close the inguinal opening 7 (cf. FIG. 12);
- a first leaf 3, disposed in an inferior and anterior manner once the prosthetic element has been put in place, tightly enclosing the spermatic cord 6 (cf. FIG. 12); this leaf extending away from the reinforcement 2 has a height which is sufficient to circumscribe the spermatic cord 6 and to permit or include a cutting 3a comprising a calibrated hole 3b for the passage of the cord 6;
- a second leaf 4, disposed in a superior manner once the prosthetic element has been put in place, extending away from the other side of the reinforcement 2, with a sufficient height to rest on the inner face of the transversalis muscle and the transversalis fascia 8 (cf. FIG. 12); this second leaf extends away from the reinforcement;
- and a third leaf 5, disposed in an inferior and posterior manner once the prosthetic element has been put in place, with a sufficient height for it to be successively folded back and held against the inner face of the superior leaf 4, and folded back against the inferior and anterior leaf 3, separating the peritoneum 10 (cf. FIG. 12) from the residual space in the anterior and inferior leaf 3, between the spermatic cord 6 and the hole 3b; this leaf too extends away from the reinforcement 2.

Each of the leaves is made of a biocompatible material which is sufficiently lacunar or porous to support in vivo a tissue implantation or growth, and sufficiently flexible to be folded back on itself and unfolded; the material is preferably a textile material, for example obtained by weaving and/or knitting a polyester filament, it being possible for this material to be covered finally with a layer of collagen.

The three leaves 3 to 5 are linked to one another via the reinforcement 2 which is common to them, and they each extend in height away from said reinforcement.

Figure 2:
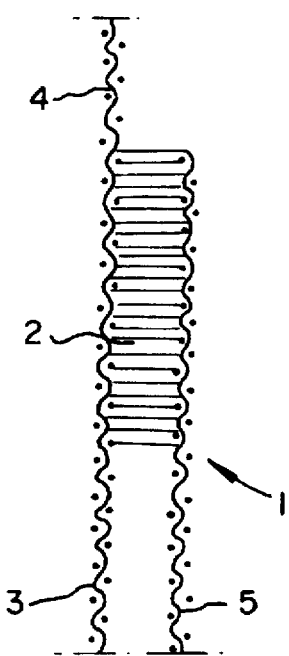
FIG. 2 represents a partial view, in vertical section, of the prosthetic element represented in FIG. 1.

In accordance with FIG. 2, the reinforcement 2 consists of a noncontiguous linking of the three leaves 3 through 5, respectively, which is obtained in particular by knitting, and thereby creating an overthickness in relation to the individual thickness of each of the three leaves.

As is shown in FIG. 1 in particular, the inferior and anterior element 3 has a continuously rounded border 3c which extends from one end of the reinforcement 2 to the other.

The dimensioning of the prosthetic element according to the invention is preferably but not exclusively the following:

width of the prosthetic element, that is to say the horizontal dimension according to FIG. 1, at least equal to 10 cm, and preferably at least equal to 15 cm;

the reinforcement 2 has a thickness at least equal to 0.1 cm, and preferably equal to 0.2 cm, and a height at least equal to 1 cm, and preferably at least equal to 2 cm;

the inferior and anterior leaf has a height (that is to say its greatest dimension) at most equal to 10 cm, and preferably at most equal to 6 cm;

the superior leaf 4 has a height at least equal to 4 cm, and preferably at least equal to 5.5 cm;

the inferior and posterior leaf has a height at least equal to 5 cm, and preferably at least equal to 7.5 cm.

Figure 3:
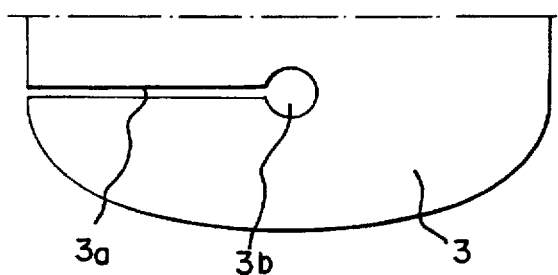
Figure 4:
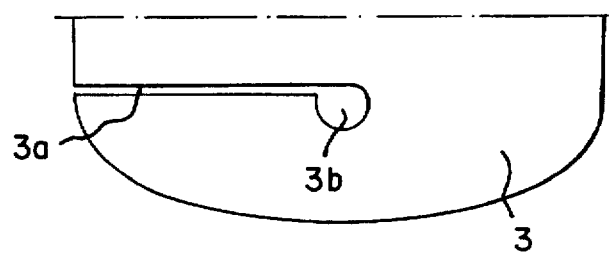
Figure 5:
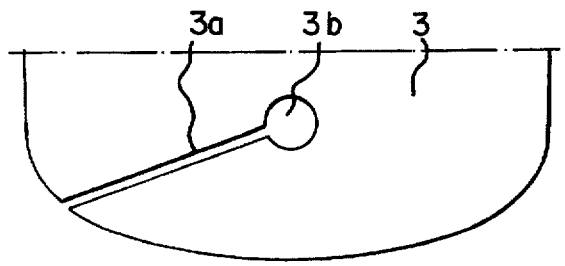

The cutting 3a in the inferior and anterior leaf 3 preferably has a form which is chosen from among the following forms, namely:

- a form which is parallel to the reinforcement 2 (cf. FIG. 3), if appropriate with a hole 3b which is offset toward or in the opposite direction from the reinforcement 2 (cf. FIG. 4);
- a form which is oblique in relation to the reinforcement 2 (cf. FIG. 5);
- a zigzagging form in front of the hole 3b (cf. FIG. 6);
- and a buttonhole form 11, in front of the hole 3b, comprising male parts 11a on one of the edges of the cutting 3a, and complementary female parts 11b on the other edge of said cutting (cf. FIG. 7).

In accordance with the representation in FIG. 8, the prosthetic element according to the invention can have a folded configuration, in accordance with which at least the leaves 4 and 5 are folded or rolled back on themselves, and on the reinforcement 2, separately or together, and are maintained in this configuration by a removable filament 9 which is interlaced between the various folds of the prosthetic element 1.

Before describing the positioning of the element which has been defined heretofore, reference will be made to FIG. 12 which shows, in a diagrammatic manner, the anatomy of the groin in which the prosthetic element according to the invention is implanted by the pre-peritoneal route, in order to treat an external oblique inguinal hernia by celioscopy; the groin in question is the left-side groin.

The following will be noted in FIG. 12:

- the iliac bone 14, on which there are attached the inguinal ligament and Cooper's ligament (which are not shown);
- the oblique 15 and transverse 16 abdominal muscles which are covered externally by the aponeurosis 17 and internally by the transversalis fascia 8, the internal inguinal opening 7 through which the spermatic cord 6 passes;
- the abdominal skin 18 linked to a layer of subcutaneous fat;
- the peritoneum 10 which contains the intestines (not shown).

An inguinal hernia is the result of the formation and passage of a peritoneal sac, under the effect of the pressure from the intestines, into the internal inguinal opening or canal 7.

In a simplified manner, a hernia of this kind is treated using a prosthetic element according to the invention, by surgery involving celioscopy, comprising the following steps;

a) as represented in FIG. 9, by means of a trocar 13, by penetration of a sterile gas by the pre-peritoneal route, the preperitoneal sac is dissected between the peritoneum 10 and the anterior parietal wall 12; two trocars 19 and 20 are likewise placed on the interior parietal wall, one of them 20 for the introduction of scissors for example, and the other 19 above and to the inside of the antero-superior iliac crest;

b) the prosthetic element 1 as described above is disposed with the inferior and posterior leaf 5 folded back and held against the inner face of the superior leaf 4, by a binding member 21 which can be absorbable (cf. FIG. 10); this prosthetic element is additionally adapted in a folded or rolled configuration, such as is represented in FIG. 8, adapted for its passage through the trocar 13;

c) the prosthetic element 1 is introduced through the trocar 13 so that it ends in the preperitoneal sac in proximity to the internal inguinal opening 7; the prosthetic element is then unfolded or opened out in the abovementioned sac;

d) as is represented in FIG. 10, the inferior and anterior leaf 3 of the prosthetic element 1 is disposed on either side of the spermatic cord 6, and then the cutting 3a is closed in an appropriate way, for example with staples;

e) the superior leaf 4 is fixed on the transversalis fascia 8, the reinforcement 2 of the prosthetic element having been positioned in front of the internal inguinal opening 7;

f) by breaking ;the binding member 21, and as is shown in FIG. 11, the inferior and posterior leaf 5 is separated from the superior leaf 4, and said inferior and posterior leaf is folded back in an anterior position separating the spermatic cord 6, and in particular the interstitial passage between the cord 6 and the hole 3b, from the peritoneum 10;

g) the preperitoneal sac is reduced by exsufflation, in such a way that the superior leaf 4 serves as a reinforcement, with or without attachment of the staple type, for the transversalis fascia, by the peritoneum 10 resting against the prosthetic element 1.

The same steps can be performed using the transperitoneal celioscopic route, with the detachment of the peritoneum being carried out from the inside of the abdominal cavity. The same prosthetic element can be implanted using traditional, open, preperitoneal surgery.

Taking into consideration the shape and the size of the inferior and anterior leaf and the inferior and posterior leaf, the indication for a prosthetic element according to the invention can be broadened to direct inguinal hernias, to crural hernias.

We claim:

1. A prosthetic element for the treatment of an inguinal hernia, comprising first, second and third leaves linked to each other by an elongate and flexible binding member and extending away from the binding member, the first, second and third leaves being formed of a biocompatable material which is adapted to support a tissue implantation or growth in vivo and to permit the leaves to fold on one another, wherein the binding member is adapted to close an inguinal opening, wherein the first leaf has a cutting including a hole defined therein for passing a spermatic cord therethrough, and is adapted to tightly enclose the spermatic cord upon passage of the spermatic cord through the hole, wherein the second leaf extends away from the first leaf and is adapted to lay on an inner face of a transversalis fascia, and wherein the third leaf is adapted to at least partially cover the first leaf having the spermatic cord passed therethrough, to at least partially separate a peritoneum from a residual space in the first leaf between the spermatic cord and the hole.

2. A prosthetic element according to claim 1, wherein the first leaf has a continuously rounded border which extends from one end of the binding member to another end of the binding member.

3. A prosthetic element according to claim 1, wherein the prosthetic element has a width of at least 10 cm.

4. A prosthetic element according to claim 1, wherein the prosthetic element has a width of at least 15 cm.

5. A prosthetic element according to claim 1, wherein the binding member has a thickness of at least 0.1 cm.

6. A prosthetic element according to claim 1, wherein the binding member has a thickness of at least 0.2 cm.

7. A prosthetic element according to claim 1, wherein the binding member has a length of at least 1 cm.

8. A prosthetic element according to claim 1, wherein the binding member has a length of at least 2 cm.

9. A prosthetic element according to claim 1, wherein the first leaf has a height of at most 10 cm.

10. A prosthetic element according to claim 1, wherein the first leaf has a height of at most 6 cm.

11. A prosthetic element according to claim 1, wherein the second leaf has a height of at least 4 cm.

12. A prosthetic element according to claim 1, wherein the second leaf has a height of at least 5.5 cm.

13. A prosthetic element according to claim 1, wherein the third leaf has a height of at least 5 cm.

14. A prosthetic element according to claim 1, wherein the third leaf has a height of at least 7.5 cm.

15. A prosthetic element according to claim 1, wherein at least two of the first, second, and third leaves and the binding member are folded about themselves to produce folds, the prosthetic element further comprising a removable filament which is interlaced in the folds and maintains the prosthetic element in a folded configuration.

16. A prosthetic element according to claim 1, wherein the cutting has a form selected from the group consisting of:

(a) parallel to the binding member;

(b) oblique in relation to the binding member;

(c) substantially Z-shaped;

(d) a buttonhole formation, having male parts on one side of the cutting and corresponding female parts on another side of the cutting.

17. A prosthetic element according to claim 1, wherein, in form (a), the hole is offset from the cutting.

18. A prosthetic element according to claim 1, wherein the binding member comprises a noncontiguous linking of the first, second and third leaves such that the binding member is thicker than any of the first, second, and third leaves.

19. A prosthetic element according to claim 1, wherein the third leaf is adapted to at least partially cover (a) the first leaf having the spermatic cord passed therethrough and (b) the spermatic cord, to at least partially separate the peritoneum from the spermatic cord.

20. A prosthetic element for the treatment of an inguinal hernia, located in a human body, comprising first, second and third leaves linked to each other by an elongate and flexible binding member and extending away from the binding member, the first, second and third leaves being formed of a biocompatable material which is adapted to support a tissue implantation or growth in vivo and to permit the leaves to fold on one another, wherein the binding member closes an inguinal opening in the body, wherein the first leaf has a cutting including a hole defined therein which has a spermatic cord passed therethrough, the spermatic cord being tightly enclosed by the first leaf, wherein the second leaf extends away from the first leaf and lays on an inner face of a transversalis fascia, and wherein the third leaf at least partially covers the first leaf having the spermatic cord passed therethrough, to at least partially separate a peritoneum from a residual space in the first leaf between the spermatic cord and the hole.

21. A prosthetic element according to claim 20, wherein the third leaf at least partially covers (a) the first leaf having the spermatic cord passed therethrough and (b) the spermatic cord, to at least partially separate the peritoneum from the spermatic cord.

* * * * *